United States Patent
Anton et al.

(10) Patent No.: US 9,498,171 B2
(45) Date of Patent: Nov. 22, 2016

(54) METHOD FOR EXAMINING AN OBJECT USING AN X-RAY RECORDING SYSTEM FOR PHASE CONTRAST IMAGING WITH DISPLACEMENT MEASUREMENT

(71) Applicant: Siemens Aktiengesellschaft, Munich (DE)

(72) Inventors: Gisela Anton, Erlangen (DE); Florian Bayer, Hemhofen (DE);
(Continued)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 162 days.

(21) Appl. No.: 14/488,392

(22) Filed: Sep. 17, 2014

(65) Prior Publication Data
US 2015/0092915 A1    Apr. 2, 2015

(30) Foreign Application Priority Data
Sep. 27, 2013   (DE) .................. 10 2013 219 554

(51) Int. Cl.
*G03H 5/00*    (2006.01)
*A61B 6/00*    (2006.01)

(52) U.S. Cl.
CPC .......... *A61B 6/4291* (2013.01); *A61B 6/4283* (2013.01); *A61B 6/4441* (2013.01); *A61B 6/484* (2013.01); *A61B 6/4233* (2013.01); *A61B 6/4458* (2013.01)

(58) Field of Classification Search
CPC .............. G21K 2207/00; G21K 1/067; G21K 2201/067; A61B 6/484; A61B 6/486;
(Continued)

(56) References Cited

U.S. PATENT DOCUMENTS

| 7,500,784 B2 | 3/2009 | Grebner et al. |
| 2009/0092227 A1 | 4/2009 | David et al. |

(Continued)

FOREIGN PATENT DOCUMENTS

DE    102010018715 A1    11/2011

OTHER PUBLICATIONS

M. Spahn, "Flat Detectors and Their Clinical Applications", European Radiology, vol. 15, 2005, 14pgs,; 2005; Apr. 2, 2005.
G. Pelzer, "Energy-Resolved Interferometric X-Ray Imaging", Proc. SPIE 8668, Medical Imaging 2013: 6pgs, Physics of Medical Imaging, 866851-1-6 (Mar. 19, 2013);; 2013.
(Continued)

*Primary Examiner* — Jurie Yun
(74) *Attorney, Agent, or Firm* — Harness, Dickey & Pierce, P.L.C.

(57) ABSTRACT

A method, for examining an object using an X-ray recording system, includes aligning the object in the X-ray beam and the X-ray recording system with one another such that regions in the X-ray beam are uncovered for measurement of a free field. During an X-ray image recording, the components are moved relative to one another with a lateral displacement. In a position of the relative lateral displacement of the components, a reference image containing free fields is recorded. The X-ray image recording is generated from partial images during the displacement and the position of the second component relative to the first component is determined for each partial recording such that the displacement distances of the displacements and the reference phases are calculated from a selected set of pixels and the measured intensity values thereof. Finally, the image information is determined from the partial images, the displacements and the reference phases.

18 Claims, 2 Drawing Sheets

(72) Inventors: Jürgen Durst, Dittenheim (DE); Thilo Michel, Nürnberg (DE); Georg Pelzer, Eggenfelden (DE); Jens Rieger, Forchheim (DE); Thomas Weber, Erlangen (DE)

(58) Field of Classification Search
CPC ........... A61B 6/54; A61B 6/545; A61B 6/547; A61B 6/587; G01N 23/04; G01N 23/20075
USPC .................................. 378/36, 62, 84, 85, 205
See application file for complete search history.

(56) References Cited

U.S. PATENT DOCUMENTS

2012/0236985 A1    9/2012   Schusser et al.
2015/0092915 A1    4/2015   Anton et al.

OTHER PUBLICATIONS

K.C. Gödel "Röntgen-Phasenkontrast-Bildgebung"; Bachelorarbeit am Pyhsikalischen Institut der Friedrich-Alexander Universität—Erlangen—Nürnberg; 2pgs; 2011; DE; Aug. 23, 2011 is: Introcuction + abstract.
U.S. Office Action for corresponding U.S. Appl. No. 14/488,379 mailed Apr. 21, 2016.

METHOD FOR EXAMINING AN OBJECT USING AN X-RAY RECORDING SYSTEM FOR PHASE CONTRAST IMAGING WITH DISPLACEMENT MEASUREMENT

PRIORITY STATEMENT

The present application hereby claims priority under 35 U.S.C. §119 to German patent application number DE 102013219554.0 filed Sep. 27, 2013, the entire contents of which are hereby incorporated herein by reference.

FIELD

At least one embodiment of the invention generally relates to a method for examining an object using an X-ray recording system for phase contrast imaging having at least one X-ray emitter for generating a quasi-coherent X-ray beam, an X-ray image detector with pixel elements arranged in a matrix, a diffraction or phase grating which is arranged between the object and the X-ray image detector, and an analyzer grating associated with the phase grating for generating an intensity pattern or interference pattern.

BACKGROUND

For a new method for stochastic phase scanning, X-ray phase contrast imaging using a Talbot-Lau apparatus, which is dealt with in a parallel application, it is necessary to measure the relative lateral distance of two components K1 and K2 from a reference position, the internal components of which are arranged fixedly in respect of one another. This measurement may be performed e.g. with an optical interferometer, but this method of measurement is difficult and prone to interference.

In the Talbot-Lau apparatus for X-ray phase contrast imaging, as described for example by Georg Pelzer et al. in "Energy-resolved interferometric X-ray imaging", published in Proc. SPIE 8668, Medical Imaging 2013: Physics of Medical Imaging, (Mar. 19, 2013) pages 866851 ff., the gratings $G_0$, $G_1$ and $G_2$ are mounted on a fixed rack. By means of a controlled lateral displacement of one of these gratings $G_0$ to $G_2$ in fractions of the grating period, for example by a piezo-stepper, an intensity distribution is scanned (phase stepping), from which the image variables absorption, phase displacement and dark field can be calculated.

An X-ray recording system, with which phase contrast imaging of the type mentioned in the introduction can be performed, is known for example from U.S. Pat. No. 7,500,784 B2, which is explained on the basis of FIG. 1.

Figure 1:
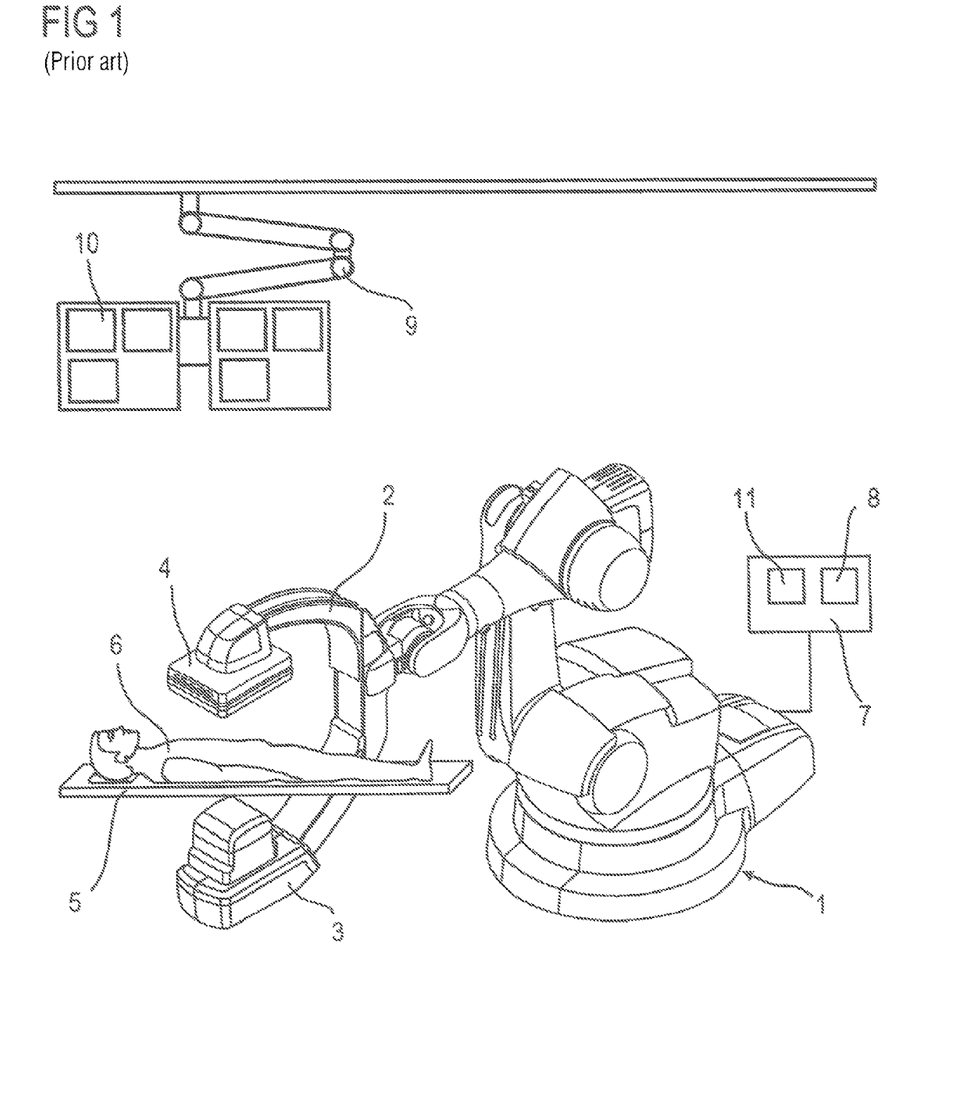
FIG. 1 shows a known C-arm angiographic system of an X-ray diagnostic device with an industrial robot as a support apparatus, FIG. 2 a schematic structure of a known Talbot-Lau interferometer for differential phase contrast imaging and FIG. 3 a schematic structure of an inventive arrangement of a Talbot-Lau interferometer.

FIG. 1 shows the typical essential features of an X-ray recording system for an interventional suite with a C-arm 2 held by a stand 1 in the form of a six-axis industrial or articulated robot, with an X-ray source, for example an X-ray emitter 3 with X-ray tube and collimator, and an X-ray image detector 4 being attached to the ends of said C-arm 2 as an image recording unit.

By way of the articulated robot known for example from U.S. Pat. No. 7,500,784 B2, which preferably has six axes of rotation and thus six degrees of freedom, the C-arm 2 can be adjusted spatially as required, being rotated for example about a center of rotation between the X-ray emitter 3 and the X-ray detector 4. The inventive angiographic X-ray system 1 to 4 is rotatable in particular about centers of rotation and axes of rotation on the C-arm plane of the X-ray image detector 4, preferably about the center point of the X-ray image detector 4 and about axes of rotation intersecting the center point of the X-ray image detector 4.

The known articulated robot has a baseframe which for example is permanently mounted on a base. To this a carousel is rotatably attached about a first axis of rotation. Attached to the carousel so as to pivot about a second axis of rotation is a robot rocker arm, to which is fixed a robot arm which can rotate about a third axis of rotation. A robot hand is attached at the end of the robot arm, so as to rotate about a fourth axis of rotation. The robot hand has a fixing element for the C-arm 2, which can pivot about a fifth axis of rotation and can rotate about a sixth axis of rotation extending perpendicular thereto.

The implementation of the X-ray diagnostic device is not dependent on the industrial robot. Normal C-arm devices can also be used.

The X-ray image detector 4 can be a rectangular or square, flat semiconductor detector that is preferably made of amorphous silicon (a-Si). Integrating and possibly counting CMOS detectors can also be used, however.

Located in the beam path of the X-ray emitter 3 on a tabletop 5 of a patient positioning couch is a patient 6 to be examined, as an examination object. On the X-ray diagnostic device a system control unit 7 is connected to a high-voltage generator for generating the tube voltage and to an image system 8 which receives and processes the image signals from the X-ray image detector 4 (operating elements are not shown, for example). The X-ray images can then be viewed on displays of a monitor bracket 10 held by means of a ceiling-mounted support system 9 which can travel lengthwise, pivot and rotate, and is height-adjustable. Also provided in the system control unit 7 is a processing circuit 11, the function of which is further described below.

Figure 2:
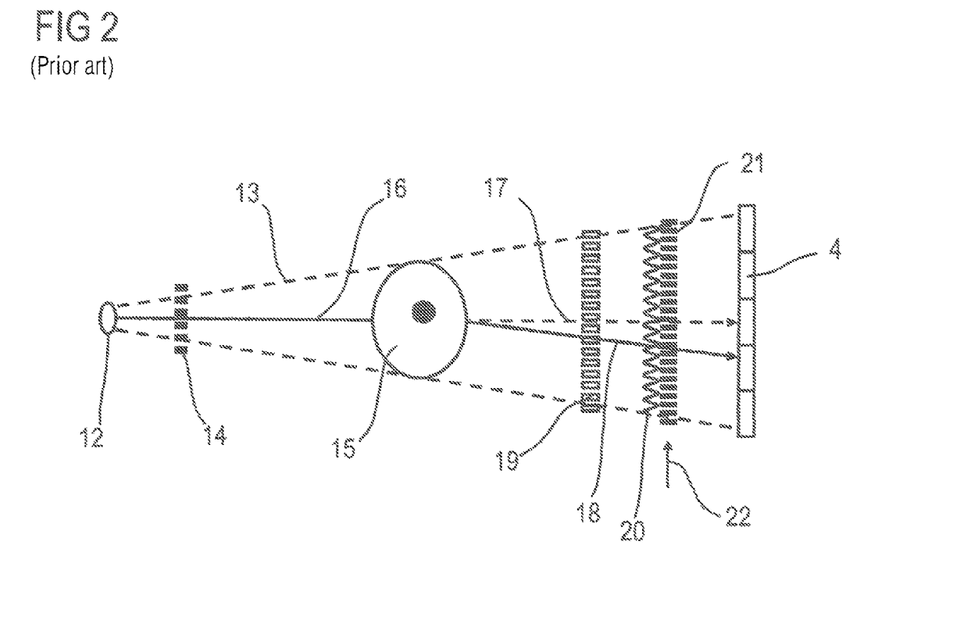

Instead of the X-ray system illustrated by way of example in FIG. 1 with the stand 1 in the form of the six-axis industrial or articulated robot, the angiographic X-ray system can, as shown in a simplified manner in FIG. 2, also have a normal ceiling- or floor-mounted bracket for the C-arm 2.

Instead of the C-arm 2 shown by way of example, the angiographic X-ray system can also have separate ceiling—and/or floor-mounted brackets for the X-ray emitter 3 and the X-ray image detector 4, which for example are electronically fixedly coupled.

In the arrangements currently being focused on for clinical phase contrast imaging, conventional X-ray tubes, currently available X-ray image detectors, as described for example by Martin Spahn [2] in "Flat detectors and their clinical applications", Eur Radiol, Vol. 15, pages 1934 to 1947, and three gratings $G_0$, $G_1$ and $G_2$ are used, as explained in greater detail below on the basis of FIG. 2, which shows a schematic structure of a Talbot-Lau interferometer for differential phase contrast imaging with expanded tube focus, gratings $G_0$, $G_1$ and $G_2$, and a pixelated X-ray image detector 4.

To generate coherent radiation the X-ray beam 13 exiting from a tube focus 12 of the non-coherent X-ray emitter 3 penetrates an absorption grating 14 ($G_0$), which produces spatial coherence of the X-ray source, as well as an examination object 15, for example the patient 6.

Because of the examination object 15 the wave front of the X-ray beam 13, which is represented by its normal 16, is deflected by phase displacement, as is made clear by the normal 17 of the wave front without phase displacement, i.e. without an object, and the normal 18 of the wave front with phase displacement. Then the phase-displaced wave front passes through a diffraction or phase grating 19 ($G_1$) with a grating constant adjusted to the typical energy of the X-ray spectrum for generating interference lines or interference patterns 20, and in turn an absorbent analyzer grating 21 ($G_2$) for reading out and capturing the interference pattern 20 generated. The grating constant of the analyzer grating 21 is adjusted to that of the phase grating 19 and of the remaining geometry of the Talbot-Lau arrangement. The analyzer grating 21 is arranged e.g. at the first or n-th Talbot distance. The analyzer grating 21 here converts the interference pattern 20 into an intensity pattern, which can be measured by the X-ray image detector 4. Typical grating constants for clinical applications are in the order of a few µm, as can also be inferred for example from the cited reference [1].

If the tube focus 12 of the beam source is sufficiently small and the radiation output generated is nevertheless sufficiently large, it may be possible to dispense with the first grating $G_0$, the absorption grating 14, as is the case if for example a plurality of field emission X-ray sources is provided as an X-ray emitter 3, as is known from DE 10 2010 018 715 A1 which is described below.

The differential phase displacement is now determined for each pixel element of the X-ray image detector 4 in that using so-called "phase stepping" 22, which is indicated by an arrow, the analyzer grating 21 $G_2$ for example is displaced in several steps by a corresponding fraction of the grating constant perpendicular to the normal 16 of the wave front of the X-ray beam 13 or 17 and laterally to the arrangement of the grating structure, and the signal $I_k$ arising for this configuration during the recording is measured in the pixel of the X-ray image detector 4 and thus the resultant interference pattern 20 is scanned. For each pixel element the parameters of a function (e.g. sine function) describing the modulation are determined by a suitable fit procedure, an adjustment or equalization procedure, to the thus measured signals $I_k$. The visibility, i.e. the standardized difference between maximum and minimum signal, is here a measurement for characterizing the quality of a Talbot-Lau interferometer. It is defined as a contrast of the scanned modulation $$V = \frac{I_{max} - I_{min}}{I_{max} + I_{min}} = \frac{A}{\bar{I}}$$

In this equation A further designates the amplitude and $\bar{I}$ the average intensity. The visibility can assume values between zero and one, since all variables are positive and $I_{max} > I_{min}$. In a real interferometer it is also the case that $I_{min} > 0$, so that the value range of V is expediently exploited. Minimum intensities greater than zero and all non-ideal properties and shortcomings of the interferometer result in a reduction in the visibility. A third item of information, which can be defined by way of the visibility and is generated by this mode of measurement, is designated as the dark field. The dark field indicates the ratio between the visibilities of measurement with an object and those without an object.

$$D = \frac{V_{obj}}{V_{ref}} = \frac{A_{obj} \cdot \bar{I}_{ref}}{A_{ref} \cdot \bar{I}_{obj}}$$

Three different images can then be generated from the comparison of particular derived variables from the fitted functions for each pixel, once with and once without an object (or patient): absorption image, differential phase contrast image (DPC) and dark field image.

SUMMARY

At least one embodiment of the invention is directed to designing an examination method such that the positions of the components K1 and K2, and therefore their relative lateral distance from one another, can be determined directly from the data from the Talbot-Lau apparatus, so that optical measurements can be dispensed with.

At least one embodiment is directed to an examination method. Advantageous embodiments are specified in the dependent claims.

At least one embodiment is directed to an examination system comprising
  X-ray image detector, phase grating and/or analyzer grating are fixedly connected to one another and form a second component,
  the object in the X-ray beam and the X-ray recording system are aligned with one another such that regions in the X-ray beam are uncovered for measurement of a free field,
  during an X-ray image recording the components are moved relative to one another with a lateral displacement by displacement distances $s_k$,
  in a starting or reference position of the relative lateral displacement of the components K1 and K2 a reference image containing free fields is recorded,
  the X-ray image recording is generated from n partial images during the displacement,
  the position of the component K2 relative to the component K1 is determined for each partial recording in that the displacement distances $s_k$ of the displacements and the reference phases $\Phi(i, j; R)$ are calculated from a selected set of pixels and the measured intensity values thereof, and
  the image information is determined from the partial images, the displacements and the reference phases $\Phi(i, j; R)$.

BRIEF DESCRIPTION OF THE DRAWINGS

The invention is described below in more detail on the basis of example embodiments shown in the drawing, in which.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing"

or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

An embodiment is directed to an examination system comprising
- X-ray image detector, phase grating and/or analyzer grating are fixedly connected to one another and form a second component,
- the object in the X-ray beam and the X-ray recording system are aligned with one another such that regions in the X-ray beam are uncovered for measurement of a free field,
- during an X-ray image recording the components are moved relative to one another with a lateral displacement by displacement distances $s_k$,
- in a starting or reference position of the relative lateral displacement of the components K1 and K2 a reference image containing free fields is recorded,
- the X-ray image recording is generated from n partial images during the displacement,
- the position of the component K2 relative to the component K1 is determined for each partial recording in that the displacement distances $s_k$ of the displacements and the reference phases $\Phi(i, j; R)$ are calculated from a selected set of pixels and the measured intensity values thereof, and
- the image information is determined from the partial images, the displacements and the reference phases $\Phi(i, j; R)$.

For X-ray phase contrast imaging using stochastic phase scanning by way of a Talbot-Lau apparatus this provides a simple measurement of the relative lateral displacement of two components K1 and K2.

It has proved to be advantageous if the X-ray emitter has, as a first component, an X-ray tube and an absorption grating permanently attached thereto for generating the quasi-coherent X-ray beam.

According to an embodiment of the invention, the image information may be information about absorption, phase and/or dark field.

Advantageously, the relative lateral displacement of the components K1 and K2 may have a linear, sinusoidal and/or continuous movement path.

According to at least one embodiment of the invention the measured intensity $I_k$ of partial recording k can be calculated from:

$I_k = I(x)$ where $x = (s_k - s_{ref})$ modulo $p_0$.

The displacement measurement may be inventively expanded if at least three components move relative to one another, of which the intensity values, displacement distances $s_k$ of the displacements and reference phases $\Phi(i, j; R)$ are determined.

Advantageously the intensity in the starting position can be calculated as follows:

$I(i,j;R) = I_0(i,j)(1 + V(i,j)\cos(\Phi(i,j;R)))$

According to an embodiment of the invention, in each of the partial images the intensity can be captured which corresponds to the intensity I(i, j; s) at a position of the interference pattern with the displacement distances s of the displacement.

It has proven to be advantageous if the intensity in each pixel with displacement distances s of the relative lateral displacement between the components K1 and K2 is determined as follows:

$I(i,j;S) = I_0(i,j)(1 + V(i,j)\cos(\Phi(i,j;R) + 2\pi s/p_0)$ where $p_0$ is the grating period length of the absorption grating.

Advantageously the displacements with a displacement distance $s_k$ and the reference phases $\Phi(i, j; R)$ can be determined from $F(\Phi(1; R), \Phi(2; R), s_k)$ using function minimization, where:

$$F(\Phi(1; R), \Phi(2; R), s_k) = \sum_{k=1}^{n} (I(1, k) - I_0(1)(1 + V(1)\cos(\Phi(1; R) + 2\pi s_k/p_0)) + I(2, k) - I_0(2)(1 + V(2)\cos(\Phi(2; R) + 2\pi s_k/p_0))).$$

According to an embodiment of the invention, from the partial recordings for each pixel the average intensity can be approximated as $$I_0(i, j) = \frac{1}{n}\sum_{k=1}^{n} I(i, j; s_k)$$

and the visibility as $$v(i, j) = (\sqrt{2} / I_0(i, j))\sqrt{\frac{1}{n}\sum_{k=1}^{n}(I(i, j; s_k) - I_0(i, j))^2}.$$

When determining the reference phase for all pixel elements the errors in the determined values can inventively be reduced by iteration and by a different selection of pixel sets.

Figure 3:
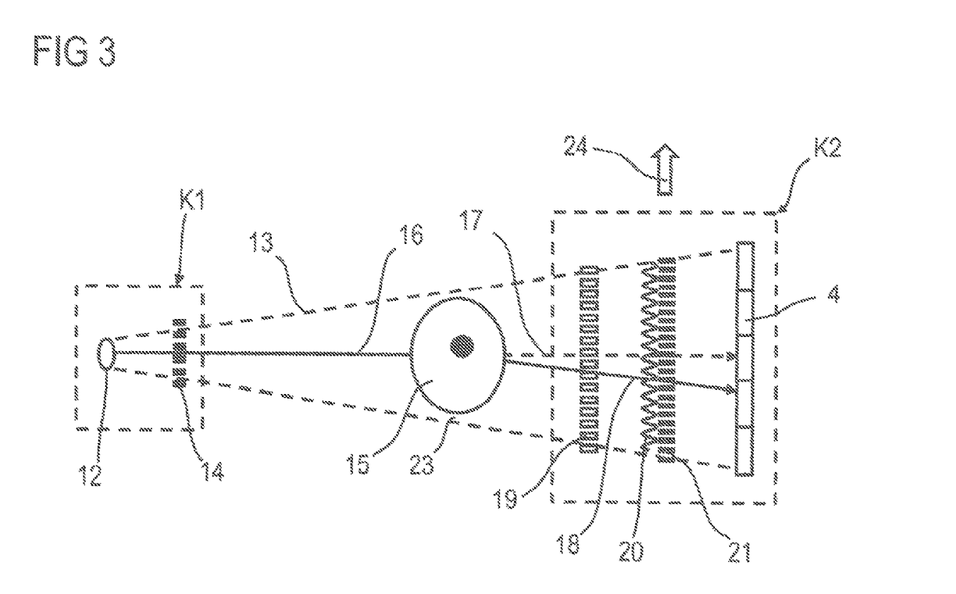

Based on FIG. 3, the circumstances of at least one embodiment in the inventive method are now explained in more detail. The structure of the Talbot-Lau apparatus is essentially the same as in FIG. 2. However, the size of the examination object 15 in the beam path of the Talbot-Lau apparatus, the X-ray beam 13, is such that there are regions on the X-ray image detector 4 in the beam path that are uncovered, at which the so-called free field can therefore be measured. These regions may for example lie at the edges or corners. This is indicated by the interspaces 23 between the peripheral rays of the X-ray beam 13 and the examination object 15.

Furthermore, the X-ray emitter 3 with its tube focus 12 and the absorption grating 14($G_0$) are permanently connected to one another to form a first component K1. Likewise the phase grating 19 ($G_1$), the analyzer grating 21 ($G_2$) and the X-ray image detector 4 are fixedly attached to one another as a second component K2.

Instead of the phase stepping 22, the displacement of the analyzer grating 21 $G_2$ in several steps by a corresponding fraction of the grating constants perpendicular to the radiation direction of the X-ray beam 13 and lateral to the arrangement of the grating structure, the components K1 and K2 are now moved relative to one another, their displacement 24 being represented by an arrow. The displacement 24 can take place continuously and have a linear, sinusoidal and/or continuous path.

With this arrangement an X-ray image recording is first taken in a starting position of the components K1 and K2, called a reference position R, with free fields, from which phase and intensity of the intensity pattern or interference pattern 20 (fringe pattern) are determined. After relative lateral displacements 24 between the components K1 and K2, in which a plurality of partial recordings are generated, the average intensity and visibility altered in each pixel are determined.

The displacements and the reference phases are calculated from a selected set of pixels and the measured intensity values thereof for example using function minimization described in greater detail below, so that a reference phase can be determined therefrom. Thus for each partial recording the relative lateral position from a pixel of the component K1 to a pixel of the component K2 is measured.

To summarize, it must be established that the object in the beam path of the Talbot-Lau apparatus must have a size and must be aligned such that there are regions in the beam path which are uncovered, in which the so-called free field can therefore be measured.

In the starting position of the relative lateral displacement 24 of the components K1 and K2, the reference position R, a phase $\Phi_0(i, j; R)$ of the fringe pattern is present in the pixels (i,j) with an intensity $$I(i,j;R) = I_0(i,j)(1+V(i,j)\cos(\Phi(i,j;R))).$$

In the case of the relative lateral displacement 24 between the components K1 and K2 with a displacement distance s the intensity in each pixel alters to:

$$I(i,j;s) = I_0(i,j)(1+V(i,j)\cos(\Phi(i,j;R)+2\pi s/p_0))$$

where $p_0$ is the grating period length of the grating displaced by the component displacement, here e.g. of the absorption grating 14 ($G_0$).

An X-ray image recording is performed in accordance with an embodiment of the method of stochastic phase scanning in several partial recordings. The number of partial recordings is expediently selected to be relatively large, approx. n>20, so that for each pixel many different phase positions with displacement distances $s_k$ are implemented in the partial recordings. The displacement distances $s_k$ of the phase positions are initially not known. From the n partial recordings the average intensity can be approximated for each pixel as $$I_0(i, j) = \frac{1}{n}\sum_{k=1}^{n} I(i, j; s_k)$$

and the visibility as $$v(i, j) = (\sqrt{2}/I_0(i, j))\sqrt{\frac{1}{n}\sum_{k=1}^{n}(I(i, j; s_k) - I_0(i, j))^2}.$$

The reference phases $\Phi(i, j; R)$ and the displacements $s_k$ must now still be determined.

The measured n intensity values $I(i, j; s_k)$ of a pixel element (i,j) are correlated with the measured intensity values of every other pixel element, because they have arisen as a result of the same set of displacement distances $s_k$. The displacement distances $s_k$ of the displacements 24 and the reference phases $\Phi(i, j; R)$ can be determined from a selected set of pixels (e.g. two pixels or more) and the intensity values $I(i, j; s_k)$ thereof. As an example with two pixel elements—indicated as 1 and 2—and twenty displacements 24, twenty-two parameters are determined from forty measured values, e.g. by minimizing the function $F(\Phi(1; R), \Phi(2; R), s_k)$ where $$F(\Phi(1; R), \Phi(2; R), s_k) =$$
$$\sum_{k=1}^{n}(I(1, k) - I_0(1)(1 + V(1)\cos(\Phi(1; R) + 2\pi s_k/p_0)) +$$
$$I(2, k) - I_0(2)(1 + V(2)\cos(\Phi(2; R) + 2\pi s_k/p_0))).$$

By taking account of each pixel in one or more sets of selected pixels, the reference phase can be determined for all pixels. The errors in the determined values can be reduced by iteration and by a different selection of pixel sets.

For each partial recording the relative lateral position of a pixel element of the component K1 to a pixel element of the component K2 can accordingly be measured. Thus although the information about the displacement only occurs using the modulus of the grating period $p_0$, it is precisely this information that is needed for the Talbot-Lau method.

The measurement for determining information about the displacement takes place for example in the processing circuit 11.

Because the apparatus can move between the free field recording and the object recording, it is necessary for some pixels not to be covered by the object, so that using their phase measurement the displacement positions of component K1 and component K2 can be correlated with one another during the free field recordings and the object recordings.

The method can also be inventively extended to more than two components which move relative to one another.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Although the invention has been illustrated and described in greater detail by the preferred example embodiment, the invention is not restricted by the disclosed examples and other variations can be derived therefrom by the person skilled in the art, without departing from the scope of protection of the invention.

What is claimed is:

1. A method for examining an object using an X-ray recording system for phase contrast imaging including at least one X-ray emitter for generating a quasi-coherent X-ray beam as a first component, an X-ray image detector including pixel elements arranged in a matrix, a diffraction or phase grating arranged between the object and the X-ray image detector, and an analyzer grating associated with the phase grating for generating an intensity pattern or interference pattern, at least two of the X-ray image detector, phase grating and analyzer grating being fixedly connected to one another and form a second component, the method comprising:

aligning the object in the X-ray beam, and the X-ray recording system, with one another such that regions in the X-ray beam are uncovered for measurement of a free field;

moving the components, during an X-ray image recording, relative to one another with a lateral displacement by displacement distances;

recording, in a starting or reference position of the relative lateral displacement of the components, a reference image containing free fields;

generating the X-ray image recording from n partial images during the displacement;

determining a position of the second component relative to the first component for each partial recording, wherein the displacement distances of the displacements and reference phases are calculated from a selected set of pixels and measured intensity values of the selected set of pixels; and determining image information from the partial images, the displacements and the reference phases.

2. The examination method of claim 1, wherein the X-ray emitter includes, as a first component, an X-ray tube and an absorption grating permanently connected to the X-ray tube for generating the quasi-coherent X-ray beam.

3. The examination method of claim 2, wherein intensity I in each pixel, in the case of displacement distances s of the relative lateral displacement between the components, is determined as follows:

$$I(i,j;S) = I_0(i,j)(1 + V(i,j)\cos(\Phi(i,j;R) + 2\pi s/p_0))$$

where $p_0$ is a grating period length of the absorption grating, R is a reference position and V represents visibility.

4. The examination method of claim 2, wherein the image information is information about at least one of absorption, phase and dark field.

5. The examination method of claim 2, wherein the relative lateral displacement of the components includes at least one of a linear, sinusoidal and continuous movement path.

6. The examination method of claim 2, wherein measured intensity $I_k$ of a partial recording k is calculated from:

$I_k=I(x)$ where $x=(s_k-s_{ref})$modulo $p_0$, $s_k$ representing the displacement distances of the displacements and the reference phases.

7. The examination method of claim 2, wherein at least three components move relative to one another, of which intensity values, displacement distances of the displacements and reference phases are determined.

8. The examination method of claim 2, wherein intensity in the starting position is calculated as follows:

$I(i,j;R)=I_0(i,j)(1+V(i,j)\cos(\Phi(i,j;R)))$,

R being a reference position and V representing visibility.

9. The examination method of claim 2, wherein, in each of the partial images, intensity is captured which corresponds to intensity at a position of the interference pattern with the displacement distance of the displacement.

10. The examination method of claim 1, wherein the image information is information about at least one of absorption, phase and dark field.

11. The examination method of claim 1, wherein the relative lateral displacement of the first and second components includes at least one of a linear, sinusoidal and continuous movement path.

12. The examination method of claim 1, wherein measured intensity $I_k$ of a partial recording k is calculated from:

$I_k=I(x)$ where $x=(s_k-s_{ref})$modulo $p_0$, $s_k$ representing the displacement distances of the displacements and the reference phases.

13. The examination method of claim 1, wherein at least three components move relative to one another, of which intensity values, displacement distances of the displacements and reference phases are determined.

14. The examination method of claim 1, wherein the intensity I in the starting position is calculated as follows:

$I(i,j;R)=I_0(i,j)(1+V(i,j)\cos(\Phi(i,j;R)))$,

R being a reference position and V representing visibility.

15. The examination method of claim 1, wherein, in each of the partial images, intensity is captured which corresponds to intensity at a position of the interference pattern with the displacement distance of the displacement.

16. The examination method of claim 1, wherein the displacements with a displacement distance $s_k$ and the reference phases $\Phi(i, j; R)$ are determined using function minimization of $F(\Phi(1; R), \Phi(2; R), s_k)$ where:

$$F(\Phi(1;R), \Phi(2;R), s_k) = \sum_{k=1}^{n}(I(1,k) - I_0(1)(1+V(1)\cos(\Phi(1;R)+2\pi s_k/p_0)) + I(2,k) - I_0(2)(1+V(2)\cos(\Phi(2;R)+2\pi s_k/p_0))).$$

R being a reference position and V representing visibility.

17. The examination method of claim 1, wherein, from the partial recordings for each pixel, average intensity is approximated as $$I_0(i,j) = \frac{1}{n}\sum_{k=1}^{n} I(i,j;s_k)$$

and visibility as $$v(i,j) = (\sqrt{2}/I_0(i,j))\sqrt{\frac{1}{n}\sum_{k=1}^{n}(I(i,j;s_k)-I_0(i,j))^2}.$$

18. The examination method of claim 1, wherein, when determining the reference phase for all pixel elements, the errors in the values determined are reducible by iteration and by a different selection of pixel sets.

* * * * *